United States Patent
Koninckx et al.

(10) Patent No.: US 8,172,788 B2
(45) Date of Patent: May 8, 2012

(54) ADHESION PREVENTION AND AN INTRA-ABDOMINAL COOLING AND INSUFFLATION ASSEMBLY THEREFOR

(75) Inventors: Philippe Koninckx, Bierbeek (BE); Thomas Koninckx, Leuven (BE)

(73) Assignee: K. U. Leuven Research and Development, Leuven (BE)

( * ) Notice: Subject to any disclaimer, the term of this patent is extended or adjusted under 35 U.S.C. 154(b) by 1327 days.

(21) Appl. No.: 11/569,932

(22) PCT Filed: Jun. 1, 2005

(86) PCT No.: PCT/BE2005/000089
§ 371 (c)(1), (2), (4) Date: Feb. 13, 2007

(87) PCT Pub. No.: WO2005/117779
PCT Pub. Date: Dec. 15, 2005

(65) Prior Publication Data
US 2008/0039911 A1 Feb. 14, 2008

(30) Foreign Application Priority Data
Jun. 1, 2004 (GB) .................................. 0412167.9

(51) Int. Cl.
*A61M 37/00* (2006.01)
*A61F 7/12* (2006.01)
(52) U.S. Cl. .............................. 604/26; 607/96; 128/898
(58) Field of Classification Search ...................... 604/26
See application file for complete search history.

(56) References Cited

U.S. PATENT DOCUMENTS

| | | | |
|---|---|---|---|
| 5,139,478 A * | 8/1992 | Koninckx et al. | 604/26 |
| 5,246,419 A | 9/1993 | Absten | |
| 6,096,068 A | 8/2000 | Dobak et al. | |
| 6,231,595 B1 | 5/2001 | Dobak et al. | |
| 6,261,312 B1 | 7/2001 | Dobak et al. | |
| 6,338,731 B1 | 1/2002 | Laufer et al. | |
| 2,040,717 A1 | 4/2002 | Dobak | |
| 2,068,964 A1 | 6/2002 | Dobak | |
| 2,091,429 A1 | 7/2002 | Dobak et al. | |
| 2,091,430 A1 | 7/2002 | Dobak et al. | |

(Continued)

FOREIGN PATENT DOCUMENTS

JP 2002-538880 11/2002

(Continued)

OTHER PUBLICATIONS

International Search Report (PCT/BE2005/000089) mailed Sep. 6, 2005.

(Continued)

*Primary Examiner* — Roy Gibson
*Assistant Examiner* — Kaitlyn Smith
(74) *Attorney, Agent, or Firm* — Clark & Elbing LLP (57) ABSTRACT

By present invention it has been found that hypothermia decreases adhesion formation more specifically pneumoperitoneum-enhanced adhesion formation. A cooling system has been designed to reduce the peritoneal cavity temperature during surgery, while maintaining at all times a 100% relative humidity in order to prevent desiccation, and a regulatory unit designed to condition the insufflated gas to achieve this while minimalising the necessary cooling. This is a new method for more effectively preventing adhesion though cooling while preventing desiccation. In mice it was demonstrated that factors such as environmental temperature, anaesthesia, ventilation and pneumoperitoneum can be used to influence body temperature in order to prevent adhesion formation.

9 Claims, 8 Drawing Sheets

U.S. PATENT DOCUMENTS

| | | | |
|---|---|---|---|
| 2,095,200 | A1 | 7/2002 | Dobak et al. |
| 2,103,519 | A1 | 8/2002 | Dobak et al. |
| 2,128,698 | A1 | 9/2002 | Dobak et al. |
| 2,169,489 | A1 | 11/2002 | Dobak et al. |
| 6,520,185 | B1 | 2/2003 | Bommannan et al. |
| 6,645,198 | B1 | 11/2003 | Bommannan et al. |
| 2002/0045892 | A1 | 4/2002 | Kramer |
| 2002/0091378 | A1 | 7/2002 | Dobak et al. |
| 2002/0156469 | A1 | 10/2002 | Yon et al. |
| 2003/0014095 | A1 | 1/2003 | Kramer et al. |
| 2004/0087934 | A1 | 5/2004 | Dobak et al. |
| 2004/0147914 | A1 | 7/2004 | Kramer |
| 2004/0220559 | A1 | 11/2004 | Kramer et al. |
| 2004/0267250 | A1 | 12/2004 | Yon et al. |

FOREIGN PATENT DOCUMENTS

| | | |
|---|---|---|
| JP | 2004-511309 | 4/2004 |
| WO | WO 00/54682 | 9/2000 |
| WO | WO 02/32486 | 4/2002 |

OTHER PUBLICATIONS

International Preliminary Report (PCT/BE2005/000089) completed Oct. 2, 2006.

Written Opinion of the International Searching Authority (PCT/BE2005/000089) completed Oct. 2, 2006.

Response to Written Communication dated Aug. 3, 2006, (PCT/BE2005/000089) as filed Sep. 3, 2006.

Reply to International Search Report issued on Sep. 6, 2005, Amendment Article 19(2) as filed Apr. 1, 2006.

English Translation of Notice of Grounds of Rejection from Japanese Patent Application No. 513625/2007, mailed Nov. 4, 2009.

Official Communication for European Patent Application No. 05 751 050.5, dated Sep. 7, 2010.

English Language Translation of Questioning for Japanese Application No. 513625/2007, mailed May 31, 2011.

* cited by examiner

FIGURE 8

ADHESION PREVENTION AND AN INTRA-ABDOMINAL COOLING AND INSUFFLATION ASSEMBLY THEREFOR

CROSS-REFERENCE TO RELATED APPLICATIONS

This application is the U.S. National Stage of International Application Ser. No. PCT/BE2005/000089, filed Jun. 1, 2005, which, in turn, claims benefit of British Patent Application Ser. No. 0412167.9, filed Jun. 1, 2004.

FIELD OF THE INVENTION

The present invention relates to adhesion formation prevention in general and to a cooling system and in particular to a system to reduce the temperature in the peritoneal cavity and to a regulatory unit permitting to obtain this cooling without dessication, and to a method for preventing adhesion formation in particular.

BACKGROUND OF THE INVENTION

Postoperative adhesion formation is a major clinical problem because of their complications, such as bowel obstruction (Ellis H Eur J Surg Supp 15-9, 1997), chronic pelvic pain (Duffy D M, DiZerega G S, J Reprod Med 41:19-26, 1996) and female infertility (Gomel V: Fertil Steril 40:607-611, 1983) and prolonged surgical time and postoperative complications (when additional surgical procedures are needed). The most common cause is prior surgery. The most frequent surgical procedures implicated in significant adhesion formation are gynecologic, cardiovascular, and general abdominal surgery. This is true for traditional surgery, as well as laparoscopic surgery.

The pathophysiological events involved in adhesion formation are well known (Holmdahl L et al, Eur J Surg Suppl 56-62, 1997 and DiZerega G S, Eur J Surg Suppl 10-16, 1997) and can be summarized as follows: A peritoneal defect will cause exudation, fibrin deposition, followed by an inflammatory reaction, fibrinolysis and complete reepithelialisation within 3 to 8 days. This rapid healing is a consequence of the regeneration of the mesothelial layer from multiple foci in the lesion and not from the borders as is found during repair of another epithelium. The direct consequence of this is that the duration of reepithelialisation is independent of the denuded area in the peritoneum. If this rapid healing process fails by an overload of fibrin (e.g. through bleeding), by a decreased fibrinolysis (e.g. as a consequence of a more severe tissue trauma), resulting in a persistent fibrin matrix (Bittinger F, J Surg Res 82:28-33, 1999), or by the presence of a prolonged inflammatory reaction (e.g. by an infection or by suture material), this will lead to prolonged fibroblast proliferation, collagen deposition, angiogenesis and ultimately adhesion formation.

Exact data on the prevalence and severity of these consequences are not available since adhesions vary with the severity of surgery, and since systematic second look laparoscopies cannot be performed for obvious ethical reasons. Adhesions occur in over 50% of patients following a laparotomy, whereas the risk of reintervention because of adhesions following a laparotomy was recently estimated at 35% within 10 years in a large survey in Scotland (Ellis H. et al, Lancet 353:1476-1480, 1999). Adhesion formation is a major problem following surgical procedures and is a frequent cause of postoperative pain and of infertility. Adhesions are the major cause of intestinal obstruction and it is estimated that following an intra-abdominal procedure, adhesions occur in some 50 to 80 percent of patients.

Thus, there is a need in the art for methods and compositions for inhibiting adhesion formation in patients.

Endoscopy also called minimal access surgery has become widely used over the last years because of clear-cut advantages of a decreased postoperative morbidity, less pain and a shorter hospitalisation. These procedures require by means of an insufflation system or an irrigation system a distension to permit visualisation. Endoscopic surgery uses a gas stream such as carbon dioxide gas ($CO_2$). Since anoxemia is a major cause and/or cofactor of adhesion formation, a gas mixture of $CO_2/O_2$ in suitable proportions has now been used to reduce adhesion formation has been proposed (U.S. Pat. No. 6,428,500).

However pneumoperitoneum, and in particular $CO_2$ pneumoperitoneum, remains a co-factor in adhesion formation.

We now have evaluated in a laparoscopic mouse model the specific effect of cooling upon adhesion formation under $CO_2$ pneumoperitoneum and $CO_2/O_2$.

First, the effect of body temperature upon basal and pneumoperitoneum-enhanced adhesion formation was evaluated in mice placed at room temperature (RT) or at 37° C. Secondly, the effect of using humidified air for ventilation upon body temperature was evaluated. Subsequently, the effect of body temperature (range: 32° C. to 37° C.) upon adhesion formation was evaluated in detail. Finally, in mice with a body temperature kept at 37° C., the pneumoperitoneum-enhanced adhesion formation by pure $CO_2$, together with the effects of adding 3% or 12% of oxygen, were confirmed.

It was surprisingly found that pneumoperitoneum-enhanced adhesion formation is much less at lower body temperatures.

A decrease in body temperature can be the consequence of anaesthesia and of desiccation when non-humidified gas is used either for ventilation or for pneumoperitoneum. We confirmed at an environmental temperature of 37° C. that the addition of 3% of oxygen to the pneumoperitoneum decreases adhesion formation and that 12% of oxygen causes more adhesions than 3%.

Moreover it was surprisingly found and clearly demonstrated that hypothermia reduces adhesion formation. A system for inducing and controlling hypothermia has been designed for prevention of adhesion prevention in mammalian, preferably human, surgery and preferably for endoscopic surgery.

DETAILED DESCRIPTION

Illustrative Embodiment of the Invention

During laparoscopy pneumoperitoneum is necessary to create a working space and $CO_2$ is generally used for safety reasons, i.e. a high solubility in water and a high exchange capacity in the lungs. $CO_2$ pneumoperitoneum is well known to cause systemic and local effects. Systemically, $CO_2$ pneumoperitoneum produces hypercarbia and acidosis (Junghans et al., 1997; Liem et al., 1996). Locally, $CO_2$ pneumoperitoneum decreases the pH (Volz et al., 1996), alters microcirculation (Taskin et al., 1998) and morphology of the mesothelial cells (Hazebroek et al., 2002; Volz et al., 1999; Suematsu et al., 2001).

In addition, during $CO_2$ pneumoperitoneum body temperature can decrease, especially when cold and dry $CO_2$ gas at high flow rates is used (Bessell et al., 1999). As can be expected from thermodynamics, this cooling effect is caused less by the gas temperature but mainly by the energy necessary to evaporate body water in order to humidify the dry $CO_2$ (Bessell et al., 1995). Indeed, cooling cannot be prevented with warm and dry gas (Bessell et al., 1995; Hazebroek et al., 2002), whereas cooling can be prevented to a large extend by cold and humidified gas (Hazebroek et al., 2002). Cooling can be fully prevented using warm and humidified gas, as shown in rats (Hazebroek et al., 2002), pigs (Bessell et al., 1995; Bessell et al., 1999; Mouton et al., 1999) and humans (Puttick et al., 1999). Effort in the art were the prevention of any cooling effect on the patient's body cavity and the place of surgery.

Pneumoperitoneum with dry and cold $CO_2$ alters the morphology of the mesothelium, i.e., destroys hexagonal pattern, reduces the microvilli (Hazebroek et al., 2002) and bulges up the cells (Volz et al., 1999; Suematsu et al., 2001). These effects of dry and cold $CO_2$ are also observed in the pleural mesothelium after thoracoscopy (Mouton et al., 1999). Whether this can be prevented by using warm and humidified gas is unclear, since both prevention (Mouton et al., 1999) and no effect (Hazebroek et al., 2002) were reported. Anyway, since the introduction of high flow insufflators for endoscopic surgery in the human (Koninckx and Vandermeersch, 1991), the $CO_2$ used became progressively warmed and humidified. The use of warm and humidified gas was claimed to reduce postoperative pain and duration of hospitalisation (Demco 2001) and to reduce intraperitoneal cytokine response (Puttick et al., 1999) and tumour growth (Nduka et al., 2002).

Over the last years $CO_2$ pneumoperitoneum became known as a cofactor in postoperative adhesion formation (Ordonez et al., 1997; Molinas and Koninckx 2000; Molinas et al., 2001). Several mechanisms seem to be involved. Firstly, mesothelial hypoxia triggering angiogenesis was suggested as a mechanism, since the effect increased with duration of pneumoperitoneum and with insufflation pressure, since similar effects were observed with helium pneumoperitoneum, since the addition of 2-4% of oxygen to both $CO_2$ and helium pneumoperitoneum decreased adhesion formation (Molinas and Koninckx 2000; Molinas et al., 2001), since this effect was absent in mice deficient for hypoxia inducible factor (HIF) (Molinas et al., 2003b), plasminogen activator 1 (PAI-1) (Molinas et al., 2003a), vascular endothelial growth factor (VEGF) and placental growth factor (PlGF) (Molinas et al., 2003c). Secondly, a role for reactive oxygen species (ROS) in the adhesion formation has been suggested (Binda et al., 2003) since ROS activity increases during both laparotomy and laparoscopy, since they are produced during the ischemia/reperfusion process and since the administration of ROS scavengers decreases adhesion formation in several animal models. Thirdly, other mechanisms could be involved such as cooling and dessication.

During pneumoperitoneum desiccation and cooling are intimately linked. Since the exact roles of desiccation and cooling upon peritoneal damage, and upon adhesion formation has not yet been studied in detail, we planned to evaluate in our laparoscopic mouse model the specific effect of cooling during $CO_2$ pneumoperitoneum upon adhesion formation.

Definitions

A pneumoperitoneum is in the meaning for a gas introduced in the abdomen of a patient to achieve exposure during laparoscopy and laparoscopic surgery. A pneumoperitoneum during lapararoscopy and laparascopic surgery can be achieved by insufflators and is in the meaning of a means to inject a gas, for instance carbon dioxide into the peritoneum to achieve exposure during lapaoscopy and laporoscopic surgery for treatment of a certain disorder. Endoscopic insufflation system is in the meaning of an endoscope comprising an insufflator.

Hypothermia is in the meaning of a body temperature or regional body temperature significantly below the normal body temperature in humans being 37° C. (98.6° F.). A moderate body temperature, which is obtainable by surface cooling, is considered to be 23-32° C. and a profound hypothermia is considered to be a body temperature or a regional body temperature of 12-20° C.

A patient is in this application is in the meaning of an animal, preferably a warm blooded animal, more preferably a mammal and most preferably a human that has been, will be or is subjected to a surgery treatment.

Results

In the first experiment (FIG. 1), mice and equipment were kept either at an environmental RT or at 37° C. Mice were exposed to 10 min ($T_{20}$ to $T_{30}$) or 60 min ($T_{20}$ to $T_{80}$) of pneumoperitoneum for basal and pneumoperitoneum-enhanced adhesion formation. During anaesthesia and ventilation only ($T_0$ to $T_{20}$), body temperature decreased from some 36.5° C. to 31° C. and from 37.5° C. to 35° C. at RT and 37° C., respectively. At RT, body temperature further decreased to 28.5° C. and to 26.5° C. at $T_{80}$ in mice with 10 min and with 60 min of pneumoperitoneum, respectively. At 37° C., body temperature remained constant up to $T_{80}$ at some 34.5° C. and 35.5° C. for 10 min and 60 min of pneumoperitoneum, respectively. Overall, body temperatures were always lower after 60 min of pneumoperitoneum than after 10 min i.e. both at RT ($p<0.0001$) and at 37° C. ($p=NS$); body temperatures also were always lower at RT than at 37° C. i.e. after both 10 min ($p<0.0001$) and 60 min ($p<0.0001$) of pneumoperitoneum (Two-way ANOVA).

Figure 1:
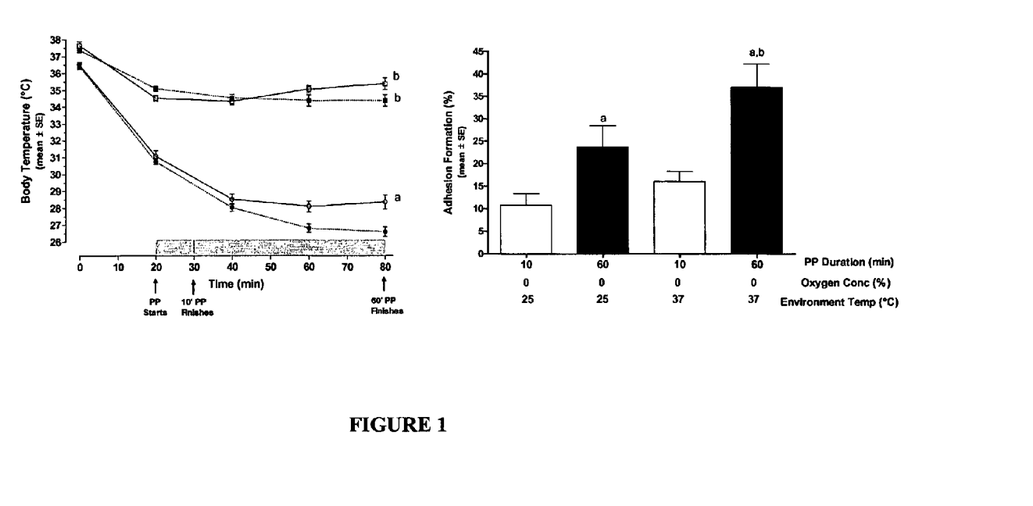
FIG. 1
Effect of environment temperature upon body temperature (left side) and upon adhesion formation (right side) in mice. Basal and pneumoperitoneum (PP)-enhanced adhesions were induced during laparoscopy at 20 cm $H_2O$ insufflation pressure and mice were kept either at RT or at 37° C.
Symbols: ○ 10 min PP, RT; ● 60 min PP, RT; □ 10 min PP, 37° C.; ■ 60 min PP, 37° C. p<0.05: $^a$10 vs. 60 min at RT or at 37° C., $^b$RT vs. 37° C. at 10 or at 60 min (Two-way ANOVA for temperature and Mann Whitney test for adhesion formation)

At RT, adhesion formation increased with the duration of pneumoperitoneum (10 min vs. 60 min: proportion: $p<0.05$), as demonstrated before. At 37° C., this effect of duration of pneumoperitoneum was more pronounced (10 min vs. 60 min: proportion: $p=0.01$, total: $p=0.04$, extent: $p=0.02$, type: $p=0.03$). In addition, at 37° C. adhesion formation was higher than at RT, clearly for pneumoperitoneum-enhanced adhesions (proportions: $p=0.04$, total: $p<0.05$, extent: $p=0.03$) and slightly for basal adhesions ($p=NS$) (FIG. 1, Table I, Mann Whitney test).

In the second experiment, body temperatures were some 1° C. higher when humidified air was used for ventilation ($p=0.003$, Two-way ANOVA), being 38.1±0.1 ($T_0$), 36.4±0.1 ($T_{10}$), 35.9±0.3 ($T_{20}$), 36.2±0.5 ($T_{30}$), 36.5±0.6 ($T_{40}$), 36.5±0.6 ($T_{50}$), 36.8±0.5 ($T_{60}$), 37.0±0.5 ($T_{70}$) and 37.1±0.5 ($T_{80}$) ° C. for humidified ventilation and 37.8±0.4 ($T_0$), 36.1±0.1 ($T_{10}$), 35.0±0.4 ($T_{20}$), 35.3±0.5 ($T_{30}$), 35.4±0.5 ($T_{40}$), 35.8±0.7 ($T_{50}$), 35.7±0.6 ($T_{60}$), 35.6±0.5 ($T_{70}$) and 36.1±0.5 ($T_{80}$) for non-humidified ventilation.

In the third experiment (FIG. 2), during anaesthesia and ventilation only ($T_0$ to $T_{20}$), body temperature decreased from 38° C. to 35.5° C. for group I and II and from 36.5° C. to 31° C. for group III. Afterwards, body temperature remained constant till $T_{80}$ at some 37° C. for group I, 36° C. for group II and 32.5° C. for group III (group I vs. III: $p<0.0001$, II vs. III: $p<0.0001$ and I vs. II: $p=0.02$). Body temperatures of groups IV, V and VI were similar to group I ($p=NS$, data not shown, Two-way ANOVA).

Figure 2:
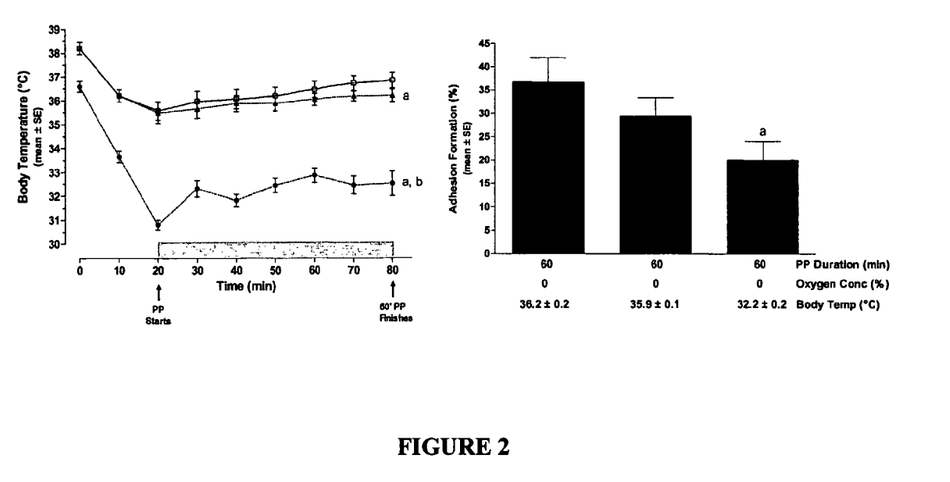
FIG. 2
Effect of body temperature (left side) upon adhesion formation (right side) in mice. Pneumoperitoneum (PP)-enhanced adhesions were induced during laparoscopy at 20 cm $H_2O$ insufflation pressure.
Symbols: □ group I, ▲ group II, ● group III. Mean±SE of body temperature during $T_{20}$-$T_{80}$ is indicated on the adhesion graph.
p<0.05: $^a$vs. group I, $^b$vs. group II (Two-way ANOVA for temperature and Mann Whitney test for adhesion formation).

Pneumoperitoneum-enhanced adhesion formation decreased with body temperature (Pearson correlation: $p=0.0171$ for proportion; FIG. 2, Table II). Compared with group I, pneumoperitoneum-enhanced adhesions were lower in group III (proportion: $p=0.04$; Mann Whitney test). Differences between the other groups failed to reach statistical significance.

Figure 3:
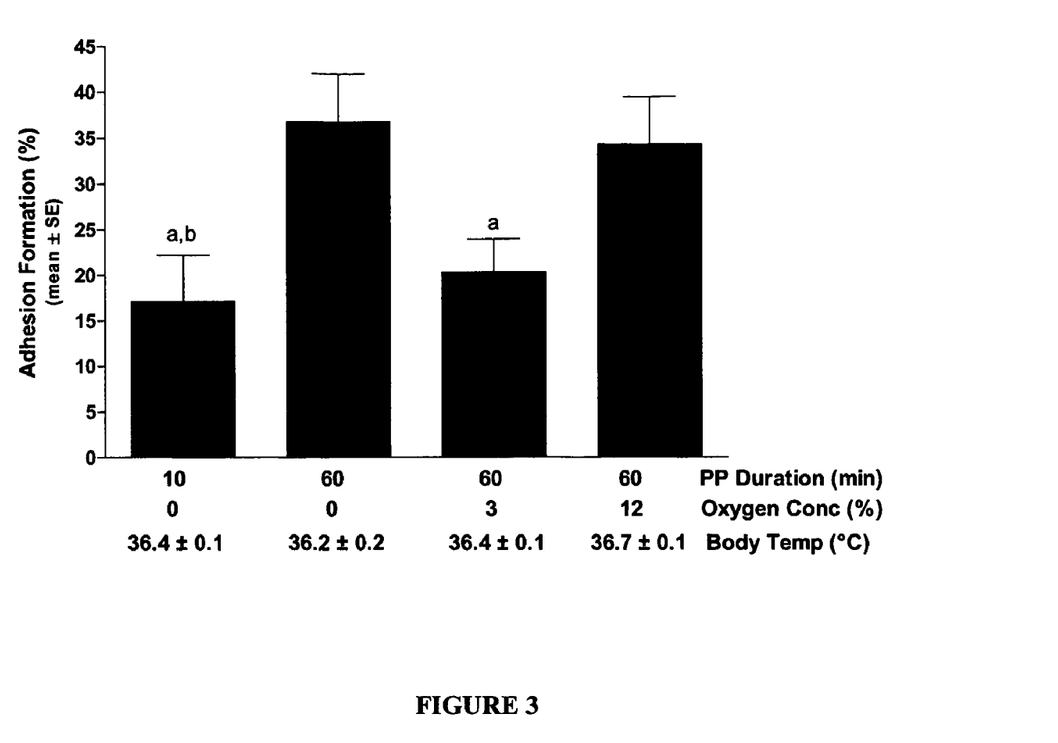
FIG. 3
Effect at 37° C. of the duration of pneumoperitoneum and of adding oxygen to the pneumoperitoneum upon adhesion formation in mice. Basal (group VI) and pneumoperitoneum (PP)-enhanced adhesions (group I, IV and V) were induced during laparoscopy at 20 cm $H_2O$ insufflation pressure with $CO_2$ containing 0% (group I and VI), 3% (group IV) or 12% of oxygen (group V). Mean±SE of body temperature during $T_{20}$-$T_{80}$ is indicated. p<0.05 $^a$vs group I, $^b$vs group V (Mann Whitney test).

As demonstrated previously (experiment I), we reconfirmed that in a 37° C. chamber, adhesion formation increased when pneumoperitoneum is prolonged from 10 to 60 min (group VI vs. I: proportion: p=0.04, total: p=0.02, extent: p=0.04, type: p=NS, tenacity: p=0.04). In comparison with pure $CO_2$ (group I), the addition of 3% oxygen to the pneumoperitoneum (group IV) decreased adhesion formation (proportion: p=0.03, total: p=0.04, extent: p<0.05, type: p=NS, tenacity: p=NS). In comparison with the addition of 3% of oxygen to the pneumoperitoneum (group IV), the addition of 12% of oxygen (group V) increased adhesions, although it failed to reach statistical significance (FIG. 3, Table II).

Figure 4:
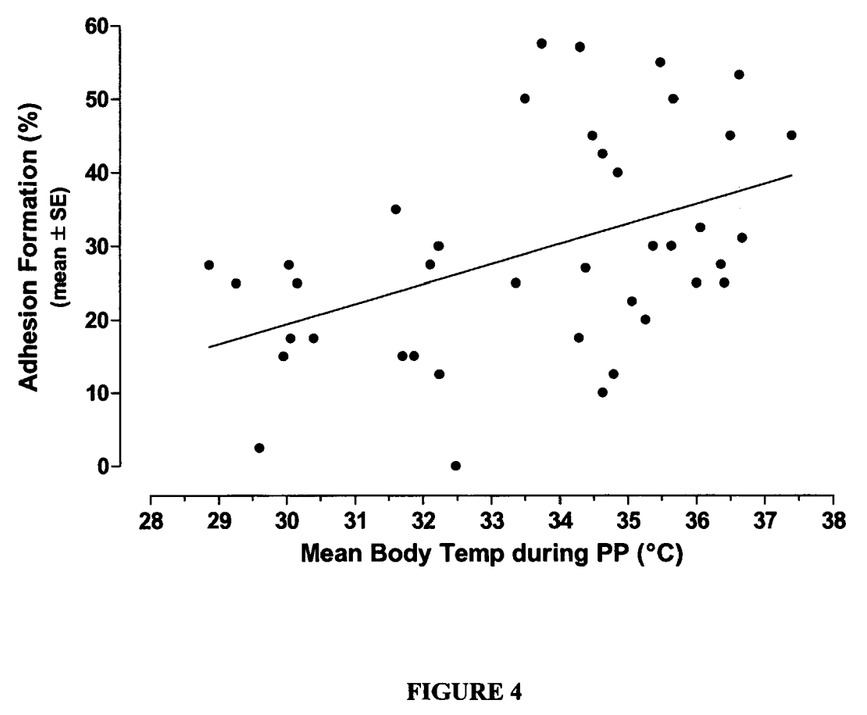
FIG. 4
Relationship between body temperature and adhesion formation. Individual values of the mean of body temperature between $T_{20}$ and $T_{80}$ with their respective proportion of adhesions are depictured for pneumoperitoneum-enhanced adhesion for experiment I and III. p=0.0036 (Pearson correlation).
Figure 5:
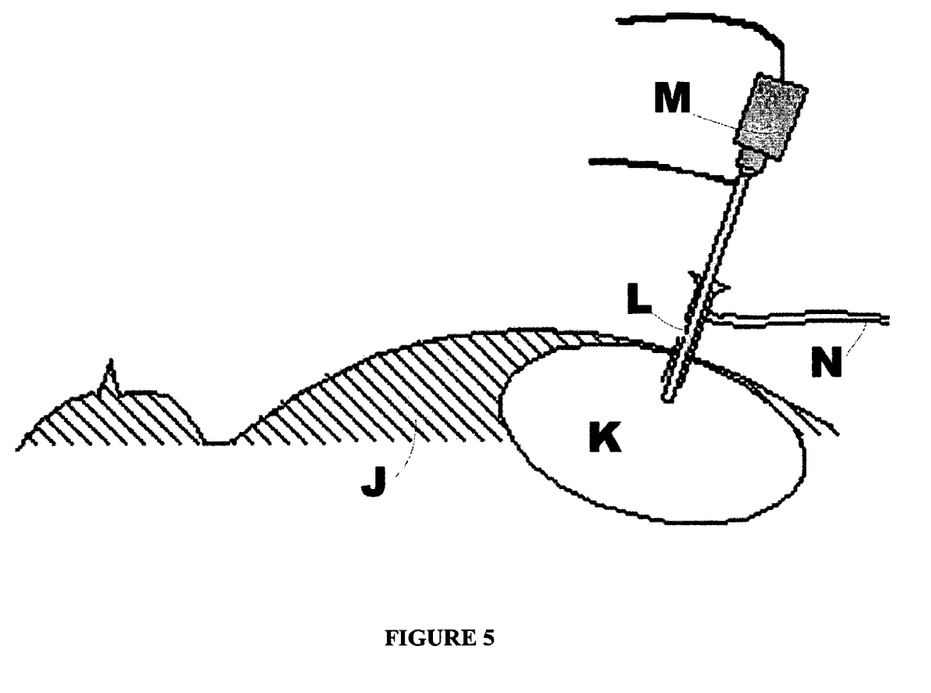
Figure 6:
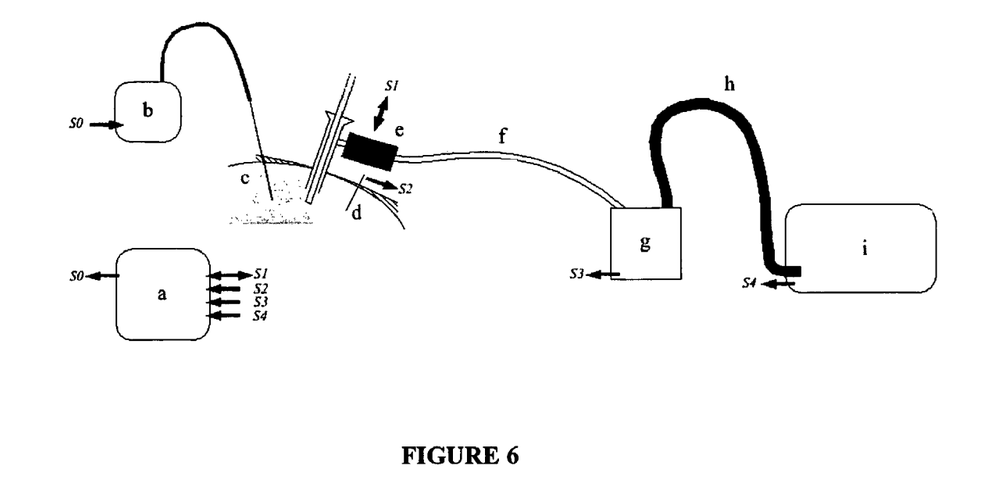
FIG. 6 is a cross-sectional side view of an assembly for intra-abdominal cooling, insufflation and humidification, wherein a=a control unit, b=an intra-abdominal cooling means, c=the intra-abdominal cooling conduit, d=an intra-abdominal temperature probe, e=a means for insufflation measurement and conditioning, f=a conditioned insufflation tubing, g=a humidifier, h=an insufflation tubing and i=an insufflator The control and measurement signals are indicated by the following symbols: S0=set point intra-abdominal cooling $t_0$; S1=the measurement of insufflation temperature $t_1$, the measurement of insufflation relative humidity $h_1$, the set point insufflation temperature $t'_1$, or the set point relative humidity $h'_1$; S2=the measurement of the intra-abdominal temperature $T_2$, S3=the demanded relative humidity $h_3$ and S4 is the insufflation flow rate r.
Figure 7:
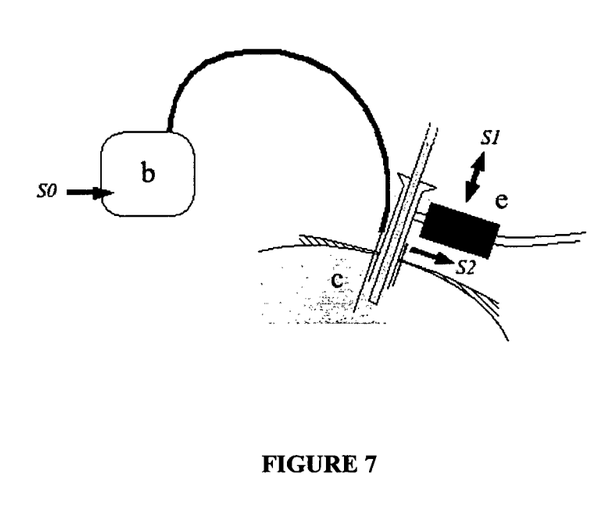
FIG. 7 is a cross-sectional side view an intra-abdominal cooling means as which can be integrated into the assembly of FIG. 5 but demonstrating that alternatively the intra-abdominal cooling can be directed via the trocar of the endoscope. b=an intra-abdominal cooling means, c=the site intra-abdominal cooling, d=an intra-abdominal temperature probe, e=a means for insufflation measurement and conditioning, The control and measurement signals are indicated by the following symbols: S0=set point intra-abdominal cooling $t_0$; S1=the measurement of insufflation temperature $t_1$, the measurement of insufflation relative humidity $h_1$, the set point insufflation temperature $t'_1$ or the set point relative humidity $h'_1$; S2=the measurement of the intra-abdominal temperature $T_2$.
Figure 8:
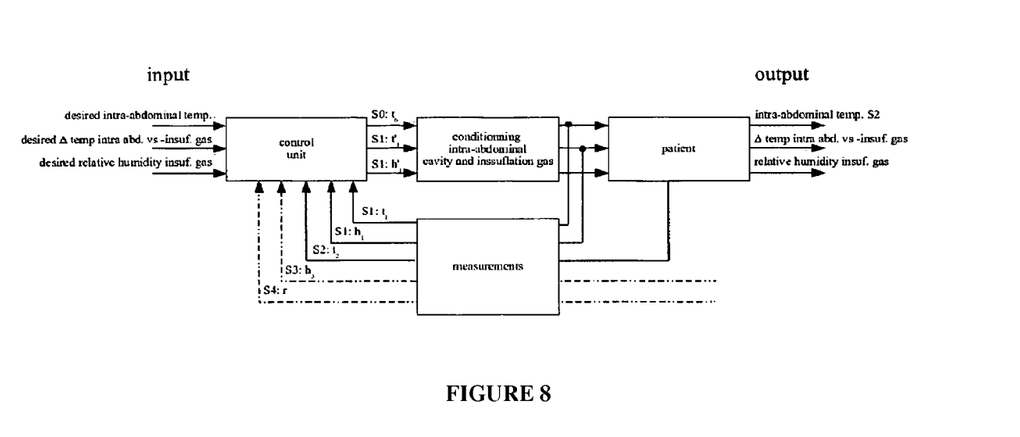
FIG. 8 is a feedback based control loop which can be used to regulate towards a desired intra abdominal temperature, the desired relative humidity of the insufflated gas and which can establish the necessary temperature difference between insufflated gas and intra abdominal temperature in order to get condensation of the insufflated gas in the abdominal cavity ensuring full humidification and preventing dessication. Optional input signals are shown as dashed lines, and comprise mainly the setpoint of the relative humidity of the humidifier and flow rate generated by the insufflator. This control mechanism is a concrete implementation of the aforementioned regulatory unit (control unit FIG. 6 a), but by no means the one and only workable solution.

In FIG. 4, the data of experiments I and III are combined in order to show graphically the relationship between body temperature and pneumoperitoneum-enhanced adhesion formation. Taken all data together, pneumoperitoneum-enhanced adhesion formation strongly decreased with lower body temperatures (Linear regression and Pearson correlation: p=0.0036 for proportion; p=0.0251 for total).

This study confirmed and extended previous data concerning of the effects of anaesthesia, ventilation and pneumoperitoneum upon body temperature.

We confirmed that anaesthesia decreases mice body temperature, as demonstrated previously in rats (Torbati et al., 2000), mice (Gardner et al., 1995) and humans (Buhre and Rossaint 2003). As expected, this cooling effect is influenced by the environmental temperature, being more pronounced at RT and less at 37° C. These observations are consistent with the reported effect of operating room temperature in humans. Indeed, patients remain normothermic after anaesthesia when they are kept in a warmer operating room, whereas they become hypothermic when placed in an operating theatre with colder temperature (Morris and Wilkey 1970; Morris 1971a; Morris 1971b). This pure anaesthetic side effect is caused by cutaneous vasodilatation, which abolishes heat conservation. Consequently, anaesthetised subjects become poikilothermic and their body temperature varies with environmental temperatures (Morris 1971b).

This study demonstrated in mice that non-humidified ventilation can decrease body temperature confirming previous data in humans (Fonkalsrud et al., 1980; Bissonnette and Sessler 1989; Dery 1973). Since unsaturated air will absorb water by evaporation from a wet surface (Williams et al., 1996), water loss from the respiratory ways is the most plausible explanation.

We previously demonstrated and confirmed in these experiments that desiccation caused by the gas used for the pneumoperitoneum causes cooling. Therefore non-humidified gas at higher flow rates causes important cooling since desiccation is important. For this reason, we took great care to prevent desiccation as much as possible by avoiding any flow through the abdomen (experiment I) and by humidifying the gas (experiment II and III). It is difficult to rule out completely at least some desiccation by the pneumoperitoneum since gas tight seals of the trocar insertions are extremely difficult to obtain and since any humidification less than 100% will cause some desiccation. This might explain that 60 min of pneumoperitoneum causes slightly more cooling than 10 min even if we tried to prevent desiccation as much as possible. These data obviously do not yet permit to rule out other simultaneous effects such as vascular compression and reduced circulation.

The relationship between desiccation and cooling is complex. First, desiccation causes cooling. Secondly, desiccation is more important at higher gas temperature since absolute humidity increases with temperature e.g. relative humidity of 100% corresponds to 25 mg of water/liter of gas at 25° C. and to 44 mg of water/liter of gas at 37° C. This might explain that the effect upon adhesion formation can be variable if not both desiccation and cooling is strictly controlled. Therefore experiments evaluating the effect of desiccation might underestimate the effect since desiccation decreases temperature which itself reduces desiccation.

By present invention we clearly demonstrated the finding that hypothermia reduces adhesion formations. Not only pneumoperitoneum-enhanced adhesions increase with the body temperature, but also the differences between basal and pneumoperitoneum-enhanced adhesion formation increases with body temperature.

Present invention demonstrates for the first time that hypothermia directly protect tissues and cells from the pneumoperitoneum adhesion enhancing effect.

One possible reason might be that oxygen consumption by cells decreases with temperature. Hypothermia decreases the global cerebral metabolic rate during ischemia, slowing the breakdown of glucose, phosphocreatine and ATP and the formation of lactate and inorganic phosphate (Erecinska et al., 2003).

Another reason for the effect of hypothermia may be its effect on the ischemia-reperfusion process, pneumoperitoneum-enhanced adhesion formation can be considered as an ischemia-reperfusion process. Hypothermia reduces the production of ROS during reperfusion in brain (Zhao et al., 1996), forebrain (Horiguchi et al., 2003), heart (Prasad et al., 1992), gut (Attuwaybi et al., 2003), endothelium (Zar and Lancaster, Jr. 2000) and muscle (Yoshioka et al., 1992). Hypothermia improves recovery of energetic parameters during reperfusion (Erecinska et al., 2003). Hypothermia also suppresses the inflammatory response after hepatic ischemia-reperfusion, decreasing the infiltration of polymorphonuclears (Patel et al., 2000), and the production of tumour necrosis factor-alpha, interleukin-1 beta and macrophage inflammatory protein-2 also decreases (Patel et al., 2000; Kato et al., 2002).

In the experiments of present application we also confirmed and extended to 37° C. our previous observations at RT which showed that the addition of 3% of oxygen to the pneumoperitoneum decreased pneumoperitoneum-enhanced adhesion formation, and that the addition of 12% of oxygen in comparison with 3% of oxygen increases adhesion formation to a similar level as with pure $CO_2$.

EXAMPLES

The example which follows explains the invention:

Animals

The study was performed in 86 female, Naval Medical Research Institute (NMRI), 9 to 10 weeks old mice weighing 30-40 g. The animals were kept under standard laboratory conditions (temperature 20°-22° C., relative humidity 50-60%, 14 hours light and 10 hours dark) at the animals' facilities of the Katholieke Universiteit Leuven. They were fed with a standard laboratory diet (Muracon. G, Carsil Quality, Turnhout, Belgium) with free access to food and water at anytime. The study was approved by the Institutional Review Animal Care Committee.

Anaesthesia and Ventilation

Animals were anaesthetised with intraperitoneal (i.p.) pentobarbital (Nembutal, Sanofi Sante Animale, Brussels, Belgium) with a dose of 0.08 mg/g. This time was considered as time 0 ($T_0$). Animal preparation started 10 min after anaesthesia ($T_{10}$). The abdomen was shaved and the animal was secured to the table in supine position. Endotracheal intubation was performed as described (Molinas et al., 2001; Molinas et al., 2003a; Molinas et al., 2003b; Molinas et al., 2003c;

Elkelani et al., 2002). Briefly, a ventilation cannula (blunt-edge 20-gauge needle; BD Microlance 3, Becton Dickinson, Fraga, Spain) was introduced in the trachea by transillumination of the vocal cords. The catheter was connected to a mechanical ventilator (Mouse Ventilator MiniVent, Type 845, Hugo Sachs Elektronik-Harvard Apparatus GmbH, March-Hugstetten, Germany) and the animal was ventilated with non-humidified or humidified room air (according to the experiment) with a tidal volume of 250 μL at 160 strokes/min until the end of the experiment ($T_{80}$).

Laparoscopic Surgery

A midline incision was performed caudal to the xyphoides appendix and a 2-mm endoscope with a 3.3-mm external sheath for insufflation (Karl Storz, Tüttlingen, Germany) was introduced into the abdominal cavity. The endoscope, connected to a video camera and light source (Karl Storz, Tüttlingen, Germany), was secured in a holder and the incision was closed gas tight around the endoscope with 5/0 polypropylene suture (Prolene, Ethicon, Johnson and Johnson Intl, Brussels, Belgium) in order to avoid leakage (Molinas et al., 2001; Molinas et al., 2003a; Molinas et al., 2003b; Molinas et al., 2003c; Elkelani et al., 2002).

The pneumoperitoneum was created after 20 min of injecting the anaesthesia ($T_{20}$) using the Thermoflator Plus (Karl Storz, Tüttlingen, Germany), which permits to add a variable concentration of $O_2$ to the $CO_2$. Insufflation gas, humidification and temperature varied with the experimental design. For humidification the Storz Humidifier 204320 33 (Karl Storz, Tüttlingen, Germany) was used. Gas temperature was determined by the ambient temperature i.e. either 23-25° C. (RT) or 37° C. Indeed, previous experiments showed equilibration of the gas temperature before some 50 cm of tubing using 7-mm inner diameter tubing and a flow rate of 2.5 L/min. The Thermoflator Plus was preset with a flow rate of 2.5 liters/min and a pressure of 18 mm Hg. A water valve was used to dampen pressure changes and to ascertain a continuous insufflation pressure of 20 cm $H_2O$ ($\cong$15 mm Hg) since any excess of $CO_2$ freely escapes from the water valve, whereas pressure is maintained accurately in the water valve.

Induction of Intraperitoneal Adhesions

After the establishment of the pneumoperitoneum ($T_{20}$), two 14-gauge catheters (Insyte-W, Vialon, Becton Dickinson, Madrid, Spain) were inserted under laparoscopic vision in both right and left flank for the working instruments. The uterus was grasped in the midline with a 1.5-mm grasper and standardized 10-mm×1.6-mm lesions were performed in the antimesenteric border of both right and left uterine horns with monopolar coagulation using a homemade 1.6-mm ball probe (10 watts, standard coagulation mode, Autocon 350, Karl Storz, Tüttlingen, Germany). In addition, identical lesions were made in both right and left pelvic sidewalls.

In order to evaluate basal and pneumoperitoneum-enhanced adhesion formation, the pneumoperitoneum was maintained for the minimum time needed to perform the surgical lesions, standardized at 10 min ($T_{20}$ to $T_{30}$), or for 60 min ($T_{20}$ to $T_{80}$), respectively (Molinas et al., 2001). The secondary ports were removed after finalizing the peritoneal lesions and the incisions were closed. All incisions were closed in a single layer with 5/0 polypropylene suture (Prolene, Ethicon, Johnson and Johnson Intl, Brussels, Belgium).

Scoring of Adhesions

A surgeon who was blinded of the group being evaluated performed a xyphopubic midline incision and a bilateral subcostal incision to explore the whole abdominal cavity during laparotomy seven days after the induction of adhesions (Molinas et al., 2001; Molinas et al., 2003a; Molinas et al., 2003b; Molinas et al., 2003c; Elkelani et al., 2002). After the evaluation of port sites and viscera, the pelvic fat tissue was carefully removed and adhesions were scored under microscopic vision using a qualitative and a quantitative scoring system. In the qualitative scoring system the following characteristics were assessed: extent (0: no adhesions; 1: 1-25%; 2: 26-50%; 3: 51-75%; 4: 76-100% of the injured surface involved, respectively), type (0: no adhesions; 1: filmy; 2: dense; 3: capillaries present), tenacity (0: no adhesions; 1: easily fall apart; 2: require traction; 3: require sharp dissection) and total (extent +type+tenacity). In the quantitative scoring system (Holmdahl et al., 1994), the proportion of the lesions covered by adhesions was measured using the following formula: adhesions (%)=(sum of the length of the individual attachments/length of the lesion)×100. The results are presented as the average of the adhesions formed at the four individual sites (right and left visceral and parietal peritoneum), which were individually scored.

Environment and Animal Temperatures

To control temperature, animals and equipment, i.e. insufflator, humidifier, water valve, ventilator and tubing, were placed in a closed chamber maintained either at RT or at 37° C. (heated air, WarmTouch, Patient Warming System, model 5700, Mallinckrodt Medical, Hazelwood, Mo., USA). Temperature of the environment was measured with Testo 645 (Testo N.V./S.A., Lenzkirch, Germany), whereas temperature of the animal was measured in the rectum with the Hewlett Packard 78353A device (Hewlett Packard, Böblingen, Germany) and recorded every 10-20 min from $T_0$ to $T_{80}$.

Experimental Design

In the first experiment (n=32), basal and pneumoperitoneum-enhanced adhesion formation, together with body temperature, were evaluated in mice placed either at RT or at 37° C. In this experiment non-humidified $CO_2$ was used for the pneumoperitoneum and special care was taken to have a gas tight seal around the trocar in order to avoid any flow through the peritoneum and thus minimize desiccation. Ventilation was performed with non-humidified air (4 groups, n=8 per group).

In the second experiment (n=6), the effect of ventilation with or without humidified air upon body temperature was evaluated in mice placed at 37° C. during 60 min of humidified $CO_2$ pneumoperitoneum (2 groups, n=3 per group).

The third experiment (n=48) was designed to evaluate in detail the effect of body temperature (range: 32° C. to 37° C.) upon adhesion formation. To achieve a body temperature with minimal cooling, i.e. around 37° C., mice were placed at 37° C. and ventilated with humidified air. To achieve a slightly lower body temperature, i.e. around 36° C., mice were placed at 37° C. and ventilated with non-humidified air. To achieve a body temperature of some 32° C., mice were placed alternatively at RT ($T_0$-$T_{20}$, $T_{30}$-$T_{40}$, $T_{50}$-$T_{60}$ and $T_{70}$-$T_{80}$) and at 37° C. ($T_{20}$-$T_{30}$, $T_{40}$-$T_{50}$ and $T_{60}$-$T_{70}$) and ventilated with humidified air. These settings were determined based on previous experiments. Pneumoperitoneum-enhanced adhesion formation was evaluated using pure and humidified $CO_2$ in mice at 37° C. (group I), 36° C. (group II) and 32° C. (group III). Pneumoperitoneum-enhanced adhesion formation at 37° C. was also evaluated using humidified $CO_2$ with 3% of oxygen (group IV) and 12% of oxygen (group V). Simultaneously, basal adhesion formation was evaluated using pure and humidified $CO_2$ (group VI). A flow of 23 ml/min through the pneumoperitoneum was used in all the groups (6 groups, n=8 per group).

Statistics

Statistical analyses were performed with GraphPad Prism version 4 for Windows 95 (GraphPad Software Inc., San Diego Calif. USA.). Mann Whitney test was used to compare adhesion formation between individual groups. Intergroup differences in body temperature were evaluated with two-way ANOVA. Linear regression and Pearson correlation were used to analyse adhesions and body temperature data. All data are presented as the mean±standard error of the mean (SE).

TABLE I

Effect of environment temperature upon adhesion formation in mice.

| Env. | Pneumoperitoneum | | Adhesion scores (mean ± SE) | | | |
|---|---|---|---|---|---|---|
| Temp | Oxygen | Duration | Extent | Type | Tenacity | Total |
| 25° C. | 0% | 10 min | 0.6 ± 0.1 | 0.6 ± 0.1 | 0.7 ± 0.1 | 1.9 ± 0.4 |
|  | 0% | 60 min | 1.0 ± 0.1 | 1.0 ± 0.2 | 0.9 ± 0.1 | 2.9 ± 0.4 |
| 37° C. | 0% | 10 min | 0.9 ± 0.1 | 0.9 ± 0.1 | 1.0 ± 0.1 | 2.8 ± 0.3 |
|  | 0% | 60 min | 1.8 ± 0.2[a,b] | 1.5 ± 0.2[a] | 1.3 ± 0.2 | 4.5 ± 0.6[a,b] |

Adhesions were induced during laparoscopy at 20 cm $H_2O$ insufflation pressure.
[a]10 vs. 60 min at RT or 37° C., $p < 0.05$,
[b]RT vs. 37° C., 10 or 60 min $p < 0.05$, Mann Whitney Test.

TABLE II

Effect of the body temperature, of the addition of oxygen to pneumoperitoneum and of the duration of pneumoperitoneum upon adhesion formation in mice.

| Group | Body Temp[b] (mean ± SE) | Pneumo-peritoneum | | Adhesion scores (mean ± SE) | | | |
|---|---|---|---|---|---|---|---|
|  |  | Oxygen | Duration | Extent | Type | Tenacity | Total |
| I | 36.2 ± 0.2° C. | 0% | 60 min | 1.7 ± 0.2 | 1.3 ± 0.1 | 1.4 ± 0.1 | 4.4 ± 0.4 |
| II | 35.9 ± 0.1° C. | 0% | 60 min | 1.4 ± 0.2 | 1.2 ± 0.3 | 1.2 ± 0.2 | 3.7 ± 0.6 |
| III | 32.2 ± 0.2° C. | 0% | 60 min | 1.0 ± 0.2 | 0.9 ± 0.2 | 1.1 ± 0.2 | 3.1 ± 0.5 |
| IV | 36.4 ± 0.1° C. | 3% | 60 min | 1.1 ± 0.2[a] | 1.1 ± 0.2 | 1.1 ± 0.1 | 3.2 ± 0.4[a] |
| V | 36.7 ± 0.1° C. | 12% | 60 min | 1.5 ± 0.2 | 1.3 ± 0.2 | 1.4 ± 0.2 | 4.1 ± 0.5 |
| VI | 36.4 ± 0.1° C. | 0% | 10 min | 0.9 ± 0.2[a] | 0.7 ± 0.2 | 0.8 ± 0.2[a] | 2.4 ± 0.6[a] |

Adhesions were induced during laparoscopy at 20 cm $H_2O$ insufflation pressure.
[a]p vs. group I <0.05, Mann Whitney Test.
[b]Body temperature during $T_{20}$-$T_{80}$ is indicated.

SUMMARY OF THE INVENTION

The present invention relates to adhesion prevention in general and to a system and a method, alone or integrated in an assembly with an endoscopic insufflation system for preventing adhesion formation in particular. Adhesion formation is a major problem following surgical procedures and is a frequent cause of postoperative pain and of infertility. Adhesions are the major cause of intestinal obstruction and it is estimated that following an intra-abdominal procedure, adhesions occur in some 50 to 80 percent of patients.

The mechanism of adhesion formation can be summarized as follows: a trauma of the peritoneal lining is rapidly followed by an inflammatory reaction; exudation of plasma, and deposition of a fibrin matrix. Subsequently the lesion is healed by the degradation of the fibrin deposition, and by proliferation of the mesenchymal lining of the peritoneum. If the repair process is not completed within a few days, fibroblast proliferation starts which ultimately will end in collagen deposition and adhesion formation. Key players in this process are in particular fibrin and fibrinolysis, macrophages and their secretion products such as growth hormones and cytokines, and obviously the epithelial repair process. From this repair process it results that adhesion formation is largely independent from the extent of the trauma.

Since by present invention it has been surprisingly found that an intra-abdominal hypothermia or an hypothermia at the side of surgery can effectively reduce post operative adhesion, since it dessication was demonstrated for the first time to enhance adhesion formation and given the known relationship between dessication and cooling, it is the aim of the present invention to provide an intra-abdominal cooling means, preferably an endoscopic system comprising the intra-abdominal cooling unit together with a humidifier and a regulatory unit permitting to achieve the desired cooling without dessication for more effectively preventing adhesion formation.

Surprisingly, it was found that cooling the tissue surface in a body cavity decreases the post-operative adhesion formation between tissue surfaces in a body cavity. The invention relates in particular to the induction of hypothermia on said tissue surfaces in said body cavity with or without a compound for the manufacture of a medicament for preventing adhesion formation. Since desiccation enhances adhesion formation whereas absolute humidity increases with temperature, it is mandatory that the insufflated gas is at all times higher than the intra-abdominal temperature in order to prevent an increase in temperature which necessarily causes a decrease in relative humidity and thus desiccation. The absolute humidity of the insufflated gas should after cooling to the intra-abdominal temperature exceed the absolute humidity at that temperature and thus cause condensation ensuring at all times a 100% relative humidity intra abdominally, thus preventing desiccation, whereas the condensated water becomes a means to deliver adhesion preventing drugs.

Given the relationship between temperature, humidity, and desiccation, a regulatory unit has been designed to optimalise the achievement of an intra-abdominal temperature decreasing from 37° C. to 32° C., together with a continuously 100% relative humidity, preferably with some condensation. Indeed the amount of cooling required in cal/min, will increase with the temperature of the insufflated gas, with the absolute humidity of this gas, and with the flow rate of the insufflation. The regulatory unit minimalises the amount of cooling by conditioning the temperature and absolute humidity of the insufflated gas. This is achieved by maintaining at all times the absolute humidity of the insufflated gas at least 1-2 mg/liter above 100% relative humidity at the intra-abdominal temperature, thus causing some condensation upon entrance in the abdominal cavity. The temperature and absolute humidity of the insufflated gas will thus vary with the intra-abdominal temperature, It is the aim of the present invention to provide a cooling system to reduce the peritoneal cavity temperature during surgery, and a method for more effectively preventing adhesion. The environmental temperature, anaesthesia, ventilation and pneumoperitoneum can be used to influence the body temperature and more particularly the temperature of the intra-abdominal surface in order to prevent adhesion formation.

An important observation is that hypothermia decreases pneumoperitoneum-enhanced adhesion formation.

This could be due to prevention from the toxic effects caused by hypoxia and the ischemia-reperfusion process. Other effects, i.e. reduction of the inflammatory response, an increase of intestinal peristaltic movements, cannot be excluded. Whether basal adhesions i.e. without a pneumoperitoneum, are also decreased by lower temperatures, is still uncertain since in our model the group of 'basal adhesions' still had 10 min of pneumoperitoneum. If substantiated in larger animals that the decrease in adhesion formation is caused by a reduction in mesothelial temperature, i.e. that a reduction in the peritoneal cavity temperature is sufficient and that the body temperature can be maintained at 37° C., the implications for the prevention of the adhesion formation in mammalian, preferably human, surgery are obvious.

The present invention involves a cooling assembly which is characterised in that it comprises an intra-luminal cooling means designed to cool a patient's body cavity or body cavity surface to a condition of hypothermia or regional hypothermia and wherein said cooling assembly comprises a cooling means (b) which is mountable to a controlling means (a) designed to regulate the intra-abdominal cooling while maintaining continuously a 95 to 100% relative humidity in the body cavity of said patient and which is mountable to a cooling conduit (c) designed to transport cooling fluid into the patient's body cavity or to a region of patient's body cavity. This assembly can be characterised in that the cooling conduit is designed to comprise a liquid fluid or to comprise a gas/liquid fluid. Moreover this assembly can be characterised in that the cooling conduit (c) is designed to sprinkle the cooling fluid into the patient's body cavity or to a region of patient's body cavity.

In a particular embodiment the assembly is characterised in that the controlling means (a) is designed to regulate the intra-abdominal cooling while maintaining continuously a relative humidity of 96 to 100%, preferably a relative humidity of 99 to 100% and most preferably a 100% humidity in patient's body cavity.

In a particular embodiment the assembly of present invention is characterised in that it is integratable with or mountable to an insufflation assembly (N) designed to induce a pneumoperitoneum in a patient's body cavity. This insufflations assembly may comprise a means for insufflation measurement and conditioning (e), an insufflation tubing (f), a humidifier (g), a humidifier (g) and an insufflator (i).

In another embodiment of present invention the assembly is characterised in that the controlling means comprises at least one sensor to measure the temperature in the patient's body cavity, at least one sensor to measure the flow rate of the insufflation fluid, at least one sensor to measure the temperature of the insufflation fluid, at least one sensor to measure the humidity of the insufflation fluid and at least one actuator to condition the temperature and absolute humidity in the insufflation fluid. It may further comprise at least one sensor to measure the flow rate in the cooling conduit.

In yet another embodiment of present invention the assembly is characterised in that the cooling conduit comprises a fluid guidance including an interior wall and an exterior wall, wherein said interior wall defines one boundary of said interior fluid guidance from a fluid inlet in said exterior wall to a fluid outlet in said exterior wall.

The present invention may also involve an embodiment of an assembly that is characterised in that controlling means is designed to condition the temperature and absolute humidity of the insufflation fluid to an absolute humidity which is slightly higher than the relative humidity at the intra-abdominal temperature. For instance the controlling means can be designed to condition the temperature and absolute humidity in the insufflation fluid to achieve an absolute humidity in said insufflation fluid which is 0.1 to 5% higher than the relative humidity at the intra-abdominal temperature.

In a particular embodiment the assembly is characterised in that the controlling means is designed to adapt the cooling rate in the body cavity to maintain a continuously 97-100% relative humidity at the desired intra-abdominal temperature. To achieve this the controlling means can be designed to maintain a temperature in the insufflation fluid which is 1° C. to 5° C. higher than the temperature in the body cavity or to maintain a temperature in the insufflation fluid which is 2° C. to 4° C. higher than the temperature in the body cavity.

In a preferred embodiment the assembly of present invention is characterised in that its controlling means is designed to regulate the temperature, humidity and/or insufflation flow rate in the cooling conduit until a predestined temperature of the intra-abdominal surface between 32-23° C. has been reached or its controlling means can be designed to regulate the temperature, humidity and or insufflation flow rate in the cooling conduit until a predestined temperature of the intraabdominal surface between 23-12° C. has been reached.

In yet another preferred embodiment the assembly can be characterised in that it cools the patient's body cavity or body cavity surface to a moderate hypothermia or that it cools the patient's body cavity or body cavity surface to a profound hypothermia In a particular embodiment the assembly is characterised in that the fluid outlet of the cooling conduit is are near the proximal end of the trocar (L) of an endoscopic surgery device and in yet another embodiment that the cooling channel is extending coaxially within the trocar (L) of an endoscopic surgery device to the distal end thereof.

The an embodiment of present invention may also involve a method to prevent or decrease post-operative adhesion formation between tissue surfaces in a body cavity, wherein the method prevents or decreases post-operative adhesion by cooling the tissue surfaces in said body cavity that is, has been or will be subjected to pneumoperitoneum and surgery, to a temperature and humidity that is effective to inhibit the formation of adhesions thereon. The method may comprise that the surfaces in a body cavity or part of the surface is cooled to a moderate hypothermia or to a profound hypothermia.

In a particular embodiment the method of present invention is further characterised in that the temperature of the insufflation fluid and absolute humidity of the insufflation fluid is conditioned to obtain an absolute humidity of the insufflation fluid that is higher than the relative humidity at the intra-abdominal temperature together for instance the temperature of the insufflation fluid and absolute humidity of the insufflation fluid can conditioned to obtain an absolute humidity of the insufflation fluid that is 0.1 to 5% higher than the intra-abdominal relative humidity.

DRAWING DESCRIPTION

Brief Description of the Drawings

FIG. 5
Displays a cross-sectional side of a patient subjected to an insufflation for endoscopy. This insufflator can be integrated with an intra-abdominal cooling means designed to obtain an intra-abdominal temperature (K) below 37° C., preferably below 35° C., ideally between 32 to 34° C., a humidification system to prevent completely dessication, and a regulatory unit permitting to obtain simultaneously cooling, and absence of dessication. J=patient, K=intra-abdominal cavity, L=trocar, N=is insufflator means and M is endoscope comprising camera and lighting

REFERENCES TO THIS APPLICATION

Attuwaybi, B. O., Hassoun, H. T., Zou, L., Kozar, R. A., Kone, B. C., Weisbrodt, N. W. and Moore, F. A. (2003) Hypothermia protects against gut ischemia/reperfusion-induced impaired intestinal transit by inducing heme oxygenase-1. *J Surg. Res.,* 115, 48-55.

Bessell, J. R., Karatassas, A., Patterson, J. R., Jamieson, G. G. and Maddern, G. J. (1995) Hypothermia induced by laparoscopic insufflation. A randomized study in a pig model. *Surg. Endosc.,* 9, 791-796.

Bessell, J. R., Ludbrook, G., Millard, S. H., Baxter, P. S., Ubhi, S. S. and Maddern, G. J. (1999) Humidified gas prevents hypothermia induced by laparoscopic insufflation: a randomized controlled study in a pig model. *Surg. Endosc.,* 13, 101-105.

Binda, M. M., Molinas, C. R. and Koninckx, P. R. (2003) Reactive oxygen species and adhesion formation: clinical implications in adhesion prevention. *Hum. Reprod.,* 18, 2503-2507.

Bissonnette, B. and Sessler, D. I. (1989) Passive or active inspired gas humidification increases thermal steady-state temperatures in anesthetized infants. *Anesth. Analg.,* 69, 783-787.

Buhre, W. and Rossaint, R. (2003) Perioperative management and monitoring in anaesthesia. *Lancet,* 362, 1839-1846.

Demco, L. (2001) Effect of heating and humidifying gas on patients undergoing awake laparoscopy. *J Am. Assoc. Gynecol. Laparosc.,* 8, 247-251.

Dery, R. (1973) Water balance of the respiratory tract during ventilation with a gas mixture saturated at body temperature. *Can. Anaesth. Soc. J.,* 20, 719-727.

Elkelani, O. A., Molinas, C. R., Mynbaev, 0. and Koninckx, P. R. (2002) Prevention of adhesions with crystalloids during laparoscopic surgery in mice. *J Am. Assoc. Gynecol. Laparosc.,* 9, 447-452.

Erecinska, M., Thoresen, M. and Silver, I. A. (2003) Effects of hypothermia on energy metabolism in Mammalian central nervous system. *J. Cereb. Blood Flow Metab,* 23, 513-530.

Fonkalsrud, E. W., Calmes, S., Barcliff, L. T. and Barrett, C. T. (1980) Reduction of operative heat loss and pulmonary secretions in neonates by use of heated and humidified anesthetic gases. *J Thorac. Cardiovasc. Surg.,* 80, 718-723.

Gardner, D. J., Davis, J. A., Weina, P. J. and Theune, B. (1995) Comparison of tribromoethanol, ketamine/acetylpromazine, Telazol/xylazine, pentobarbital, and methoxyflurane anaesthesia in HSD:ICR mice. *Lab Anim Sci.,* 45, 199-204.

Hazebroek, E. J., Schreve, M. A., Visser, P., De Bruin, R. W., Marquet, R. L. and Bonjer, H. J. (2002) Impact of temperature and humidity of carbon dioxide pneumoperitoneum on body temperature and peritoneal morphology. *J Laparoendosc. Adv. Surg. Tech. A,*12, 355-364.

Holmdahl, L., al Jabreen, M. and Risberg, B. (1994) Experimental models for quantitative studies on adhesion formation in rats and rabbits. *Eur. Surg. Res.,* 26, 248-256.

Horiguchi, T., Shimizu, K., Ogino, M., Suga, S., Inamasu, J. and Kawase, T. (2003) Postischemic hypothermia inhibits the generation of hydroxyl radical following transient forebrain ischemia in rats. *J Neurotrauma,* 20, 511-520.

Junghans, T., Bohm, B., Grundel, K. and Schwenk, W. (1997) Effects of pneumoperitoneum with carbon dioxide, argon, or helium on hemodynamic and respiratory function. *Arch. Surg.,* 132, 272-278.

Kato, A., Singh, S., McLeish, K. R., Edwards, M. J. and Lentsch, A. B. (2002) Mechanisms of hypothermic protection against ischemic liver injury in mice. *Am. J Physiol Gastrointest. Liver Physiol.,* 282, G608-G616.

Koninckx, P. R. and Vandermeersch, E. (1991) The persufflator: an insufflation device for laparoscopy and especially for CO2-laser-endoscopic surgery. *Hum. Reprod.,* 6, 1288-1290.

Liem, T. K., Krishnamoorthy, M., Applebaum, H., Kolata, R., Rudd, R. G. and Chen, W. (1996) A comparison of the hemodynamic and ventilatory effects of abdominal insufflation with helium and carbon dioxide in young swine. *J Pediatr. Surg.,* 31, 297-300.

Molinas, C. R., and Koninckx, P. R. (2000) Hypoxaemia induced by CO(2) or helium pneumoperitoneum is a cofactor in adhesion formation in rabbits. *Hum. Reprod.,*15, 1758-1763.

Molinas, C. R., Mynbaev, O., Pauwels, A., Novak, P. and Koninckx, P. R. (2001) Peritoneal mesothelial hypoxia during pneumoperitoneum is a cofactor in adhesion formation in a laparoscopic mouse model. *Fertil. Steril.,* 76, 560-567.

Molinas C. R., Elkelani O., Campo R., Luttun A., Carmeliet P. and Koninckx P. R. (2003a) Role of the plasminogen system in basal adhesion formation and carbon dioxide pneumoperitoneum-enhanced adhesion formation after laparoscopic surgery in transgenic mice. *Fertil. Steril.,* 80, 184-192.

Molinas, C. R., Campo, R., Elkelani, O. A., Binda, M. M., Carmeliet, P. and Koninckx, P. R. (2003b) Role of hypoxia inducible factors 1 alpha and 2alpha in basal adhesion formation and in carbon dioxide pneumoperitoneum-enhanced adhesion formation after laparoscopic surgery in transgenic mice. *Fertil. Steril.,* 80 Suppl 2, 795-802.

Molinas, C. R., Campo, R., Dewerchin, M., Eriksson, U., Carmeliet, P. and Koninckx, P. R. (2003c) Role of vascular endothelial growth factor and placental growth factor in basal adhesion formation and in carbon dioxide pneumoperitoneum-enhanced adhesion formation after laparoscopic surgery in transgenic mice. *Fertil. Steril.,* 80 Suppl 2, 803-811.

Morris, R. H. (1971a) Influence of ambient temperature on patient temperature during intraabdominal surgery. *Ann. Surg.,* 173, 230-233.

Morris, R. H. (1971b) Operating room temperature and the anesthetized, paralyzed patient. *Arch. Surg.,* 102, 95-97.

Morris, R. H. and Wilkey, B. R. (1970) The effects of ambient temperature on patient temperature during surgery not involving body cavities. *Anesthesiology,* 32, 102-107.

Mouton, W. G., Bessell, J. R., Pfitzner, J., Dymock, R. B., Brealey, J. and Maddern, G. J. (1999) A randomized controlled trial to determine the effects of humidified carbon dioxide insufflation during thoracoscopy. *Surg. Endosc.,* 13, 382-385.

Nduka, C. C., Puttick, M., Coates, P., Yong, L., Peck, D. and Darzi, A. (2002) Intraperitoneal hypothermia during surgery enhances postoperative tumor growth. *Surg. Endosc.,* 16, 611-615.

Ordonez, J. L., Dominguez, J., Evrard, V. and Koninckx, P. R. (1997) The effect of training and duration of surgery on adhesion formation in the rabbit model. *Hum. Reprod.,* 12, 2654-2657.

Patel, S., Pachter, H. L., Yee, H., Schwartz, J. D., Marcus, S. G. and Shamamian, P. (2000) Topical hepatic hypothermia attenuates pulmonary injury after hepatic ischemia and reperfusion. *J Am. Coll. Surg.,* 191, 650-656.

Prasad, M. R., Liu, X., Rousou, J. A., Engelman, R. M., Jones, R., George, A. and Das, D. K. (1992) Reduced free radical generation during reperfusion of hypothermically arrested hearts. *Mol. Cell Biochem.,* 111, 97-102.

Puttick, M. I., Scott-Coombes, D. M., Dye, J., Nduka, C. C., Menzies-Gow, N. M., Mansfield, A. O. and Darzi, A. (1999) Comparison of immunologic and physiologic effects of CO2 pneumoperitoneum at room and body temperatures. *Surg. Endosc.,* 13, 572-575.

Suematsu, T., Hirabayashi, Y., Shiraishi, N., Adachi, Y., Kitamura, H. and Kitano, S. (2001) Morphology of the murine peritoneum after pneumoperitoneum vs laparotomy. *Surg. Endosc.,* 15, 954-958.

Taskin, O., Buhur, A., Birincioglu, M., Burak, F., Atmaca, R., Yilmaz, I. and Wheeler, J. M. (1998) The effects of duration of CO2 insufflation and irrigation on peritoneal microcirculation assessed by free radical scavengers and total glutathion levels during operative laparoscopy. *J Am. Assoc. Gynecol. Laparosc.,* 5, 129-133.

Torbati, D., Camacho, M. T., Raszynski, A., Sussmane, J. B., Totapally, B. R., Hultquist, K. and Wolfsdorf, J. (2000) Effect of hypothermia on ventilation in anesthetized, spontaneously breathing rats: theoretical implications for mechanical ventilation. *Intensive Care Med.,* 26, 585-591.

Volz, J., Koster, S., Spacek, Z. and Paweletz, N. (1999) Characteristic alterations of the peritoneum after carbon dioxide pneumoperitoneum. *Surg. Endosc.,* 13, 611-614.

Volz, J., Koster, S., Weiss, M., Schmidt, R., Urbaschek, R., Melchert, F. and Albrech,t M. (1996) Pathophysiologic features of a pneumoperitoneum at laparoscopy: a swine model. *Am. J. Obstet. Gynecol.,* 174, 132-140.

Williams, R., Rankin, N., Smith, T., Galler, D. and Seakins, P. (1996) Relationship between the humidity and temperature of inspired gas and the function of the airway mucosa. *Crit Care Med.*, 24, 1920-1929.

Yoshioka, T., Shires, G. T. and Fantini, G. A. (1992) Hypothermia relieves oxidative stress in reperfused skeletal muscle following partial ischemia. *J. Surg. Res.*, 53, 408-416.

Zar, H. A. and Lancaster, J. R., Jr. (2000) Mild hypothermia protects against postischemic hepatic endothelial injury and decreases the formation of reactive oxygen species. *Redox. Rep.*, 5, 303-310.

Zhao, W., Richardson, J. S., Mombourquette, M. J., Weil, J. A., Ijaz, S. and Shuaib, A. (1996) Neuroprotective effects of hypothermia and U-78517F in cerebral ischemia are due to reducing oxygen-based free radicals: an electron paramagnetic resonance study with gerbils. *J. Neurosci. Res.*, 45, 282-288.

The invention claimed is:

1. A cooling and humidification assembly to cool and humidify a patient's abdominal cavity while preventing desiccation, comprising:
    an intra-abdominal cooling system (b) designed to cool a patient's abdominal cavity or abdominal cavity surface to a condition of hypothermia between 23° C. and 35° C., wherein said cooling system (b) is mountable to a cooling conduit (c) designed to transport cooling fluid into the patient's abdominal cavity,
    an insufflation assembly for administering insufflation gas with a temperature that is 1° C. to 5° C. higher than the temperature in the abdominal cavity,
    wherein said assembly further comprises a controlling means (a) to regulate the intra-abdominal cooling and humidification, maintaining continuously a 95% to 100% relative humidity in the abdominal cavity of said patient and maintaining a temperature in the insufflation gas which is 1° C. to 5° C. higher than the temperature in the abdominal cavity.

2. The cooling and humidification assembly of claim 1, wherein the controlling means comprises:
    at least one sensor to measure the temperature in the patient's abdominal cavity,
    at least one sensor to measure the flow rate of the insufflation gas,
    at least one sensor to measure the temperature of the insufflation gas,
    at least one sensor to measure the humidity of the insufflation gas, and
    at least one actuator to condition the temperature to a temperature in the insufflation gas that is 1° C. to 5° C. higher than the temperature in the abdominal cavity and to condition absolute humidity in the insufflation gas to a value that is between 95% to 100% relative humidity in the abdominal cavity of said patient.

3. The cooling and humidification assembly of claim 2, wherein the controlling means further comprises at least one sensor to measure the flow rate in the cooling conduit.

4. A method to prevent or decrease post-operative adhesion formation between tissue surfaces in an abdominal cavity, which method comprises:
    cooling the tissue surfaces in said abdominal cavity to a condition of hypothermia between 23° C. and 35° C.,
    measuring the temperature of said tissue surfaces of said abdominal cavity,
    administering an insufflation gas to said abdominal cavity, wherein:
    the temperature of said insufflation gas is adjusted to a value between 1° C. and 5° C. higher than said temperature of said tissue surfaces of said abdominal cavity, and wherein
    the absolute humidity of said insufflation gas is adjusted to a value that is higher than said intra-abdominal 100% relative humidity at said body temperature.

5. The method of claim 4, wherein said abdominal cavity is contacted with a cooling and humidification assembly comprising an intra-abdominal cooling system (b) designed to cool a patient's abdominal cavity or abdominal cavity surface to a condition of hypothermia,
    wherein said cooling system (b) is mountable to a cooling conduit (c) designed to transport cooling fluid into the patient's abdominal cavity, and
    wherein said cooling and humidification assembly, further comprises a controlling means (a) to regulate the intra-abdominal cooling and humidification, maintaining continuously a 95% to 100% relative humidity in the abdominal cavity of said patient and maintaining a temperature in the insufflation gas which is 1° C. to 5° C. higher than the temperature in the abdominal cavity.

6. The method according to claim 5, wherein the cooling fluid is a liquid fluid.

7. The method according to claim 5, wherein the cooling fluid is a gas/liquid fluid.

8. The method according to claim 4, wherein the absolute humidity in said insufflation gas is 0.1% to 5% higher than the absolute humidity at the intra-abdominal temperature.

9. The method according to claim 4 wherein a temperature in the insufflation gas is maintained which is 2° C. to 4° C. higher than the temperature in the abdominal cavity.

* * * * *